United States Patent [19]

Chang et al.

[11] 4,434,299

[45] Feb. 28, 1984

[54] PRODUCTION OF AROMATIC AMINES USING CRYSTALLINE SILICATE CATALYSTS

[75] Inventors: Clarence D. Chang, Princeton, N.J.; William H. Lang, Richmond, Vt.

[73] Assignee: Mobil Oil Corporation, New York, N.Y.

[21] Appl. No.: 440,927

[22] Filed: Nov. 12, 1982

[51] Int. Cl.³ .................... C07C 85/06; C07C 85/02
[52] U.S. Cl. .................... 564/396; 564/397; 564/402; 564/446; 564/447
[58] Field of Search .......... 564/396, 397, 402, 446, 564/447

[56] References Cited

U.S. PATENT DOCUMENTS

| | | |
|---|---|---|
| 2,780,647 | 2/1957 | Spiegler ........................ 556/402 |
| 3,551,486 | 12/1970 | Solomon et al. ................ 556/446 |
| 3,553,268 | 1/1971 | Solomon et al. ................ 556/397 |
| 3,976,697 | 8/1976 | Kuntschik et al. ............. 564/446 X |
| 4,152,353 | 5/1979 | Habermann .................... 556/446 X |
| 4,229,374 | 10/1980 | Slaugh et al. ................. 556/397 |
| 4,380,669 | 4/1983 | Chang et al. .................. 564/402 |

Primary Examiner—Paul F. Shaver
Attorney, Agent, or Firm—Alexander J. McKillop; Charles J. Speciale

[57] ABSTRACT

A process for the preparation of aniline by reaction of alicyclic alcohols or ketones with ammonia in the presence of a crystalline silicate catalyst having the structure of ZSM-5. Especially preferred alicyclic charge stocks are the mononuclear naphthenic type compounds such as cyclohexanol and cyclohexanone or mixtures thereof.

8 Claims, No Drawings

PRODUCTION OF AROMATIC AMINES USING CRYSTALLINE SILICATE CATALYSTS

BACKGROUND OF THE INVENTION

1. Field of the Invention

This invention relates to a process for the production of aromatic amines such as aniline by reaction of an alicyclic alcohol or ketone with ammonia in the presence of a crystalline silicate catalyst.

2. Description of the Prior Art

The reaction of alcohols and ketones with ammonia in the vapor phase to produce amines is well known. One usually gets a mixture of primary, secondary and tertiary amines and water. The proportion of the various amines produced can be varied somewhat by the ratio of alcohol or ketone to ammonia in the feed, i.e., large ratios give tertiary amines while low ratios tend to give primary amines. Temperatures of 300°–500° C. and pressures of 10–200 atmospheres have been employed in carrying out such reactions in the presence of various catalysts, such as alumina. Aluminum phosphate has been used as a catalyst to prepare isopropyl amines from ammonia and isopropyl alcohol at 200 atm pressure and a temperature of 350° C. This reaction is described in British Pat. No. 649,980. Amines have also been produced from alcohols, ammonia and hydrogen over hydrogenation catalysts. It has been reported that mono-, di-, and tributylamines have been prepared from n-butyl alcohol, ammonia and hydrogen at 190° C. over a pelletized nickel catalyst. U.S. Pat. No. 4,191,709 discloses a process for the preparation of an amine by reaction of methanol with ammonia in the presence of zeolite FU-1 catalyst. U.S. Pat. No. 4,229,374 describes a process for making tertiary amines by reacting alicyclic alcohols, aldehydes or ketones with ammonia. The catalyst comprises copper, tin and alkali metal supported on a suitable carrier such as alumina. U.S. Pat. No. 4,082,805 discloses the reaction of a $C_1$–$C_5$ alcohol or ether with ammonia in the presence of a ZSM-5 type zeolite catalyst.

SUMMARY OF THE INVENTION

This invention provides a process for producing aromatic amines such as aniline by reacting alicyclic alcohols or ketones with ammonia in the presence of a specific catalyst by replacing the hydrogen on the reactant ammonia with the hydrocarbon moiety of the reactant alcohol or ketone. The catalyst comprises a crystalline silicate zeolite suitably provided with a metal promoter having dehydrogenation activity. This catalyst has the advantage of being shape-selective for the production of aniline while suppressing the formation of undesirable by-products such as diphenylamine and carbazole.

The present process comprises contacting the noted reactants in the presence of the specified catalyst at a temperature within the approximate range of 150° to 650° C. and preferably between about 175° C. and about 250° C. The pressure during reaction is generally between atmospheric and 1000 psig and the relative feed rates expressed as liquid hourly space velocity of (1) alicyclic alcohol or ketone and (2) ammonia are within the approximate range of 1:1 to 5:1 and preferably between about 2:1 to 4:1.

The reaction product comprises a mixture of aniline with secondary and tertiary aromatic amines which can either be collected as a combined amine product or separated into the respective mono, secondary and tertiary components. In general, the secondary and tertiary amines comprise a smaller fraction of the reaction products as the size and molecular weight of the alcohol or ketone reactant increases. The general reaction may be illustrated as follows:

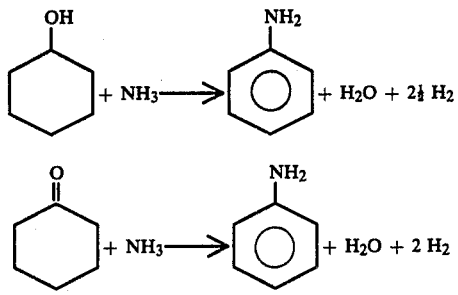

DESCRIPTION OF SPECIFIC EMBODIMENTS

The catalyst employed in this invention is prepared by compositing a hydrogenation/dehydrogenation component with a particular crystalline silicate zeolite. Compositing may be effected by ion-exchange of the zeolite, by impregnation of the zeolite or by other means which lead to an intimate association of the hydrogenation/dehydrogenation component with the zeolite.

The particular crystalline zeolite utilized herein may be any member of the novel class of zeolites now to be described. Although these zeolites have unusually low alumina contents, i.e., high silica to alumina ratios, they are very active even when the silica to alumina ratio exceeds 30. The activity is surprising since catalytic activity is generally attributed to framework aluminum atoms and/or cations associated with these aluminum atoms. These zeolites retain their crystallinity for long periods in spite of the presence of steam or high temperature which induces irreversible collapse of the framework of other zeolites, e.g., of the X and A type. Furthermore, carbonaceous deposits, when formed, may be removed by burning at higher than usual temperatures to restore activity. These zeolites, used as catalysts, generally have low coke-forming activity and therefore are conducive to long times on stream between regenerations by burning with oxygen-containing gas such as air.

An important characteristic of the crystal structure of this class of zeolites is that it provides constrained access to and egress from the intracrystalline free space by virtue of having an effective pore size intermediate between the small pore Linde A and the large pore Linde X, i.e., the pore windows of the structure have about a size such as would be provided by 10-membered rings of oxygen atoms. It is to be understood, of course, that these rings are those formed by the regular disposition of the tetrahedra making up the anionic framework of the crystalline aluminosilicate, the oxygen atoms themselves being bonded to the silicon or aluminum atoms at the centers of the tetrahedra. Briefly, the preferred type zeolites useful in this invention possess, in combination: a silica to alumina mole ratio of at least about 12; and a structure providing constrained access to the crystalline free space.

The silica to alumina ratio referred to may be determined by conventional analysis. This ratio is meant to represent, as closely as possible, the ratio in the rigid anionic framework of the zeolite crystal and to exclude aluminum in the binder or in cationic or other form within the channels. Although zeolites with a silica to alumina ratio of at least 12 are useful, it is preferred to use zeolites having higher ratios of at least about 30. Such zeolites, after activation, acquire an intracrystalline sorption capacity for normal hexane which is greater than that for water, i.e., they exhibit "hydrophobic" properties. It is believed that this hydrophobic character is advantageous in the present invention.

The zeolites useful in this invention have an effective pore size such as to freely sorb normal hexane. In addition, the structure must provide constrained access to larger molecules. It is sometimes possible to judge from a known crystal structure whether such constrained access exists. For example, if the only pore windows in a crystal are formed by 8-membered rings of oxygen atoms, then access by molecules of larger cross-section than normal hexane is excluded and the zeolite is not of the desired type. Windows of 10-membered rings are preferred, although in some instances excessive puckering of the rings or pore blockage may render these zeolites ineffective. 12-membered rings usually do not offer sufficient constraint to produce the advantageous conversions, although the puckered 12-ring structure of TMA offretite shows constrained access. Other 12-ring structure may exist which, due to pore blockage or to other cause, may be operative.

Rather than attempt to judge from crystal structure whether or not a zeolite possesses the necessary constrained access to molecules larger than normal paraffins, a simple determination of the "Constraint Index" as herein defined may be made by passing continuously a mixture of an equal weight of normal hexane and 3-methylpentane over a small sample, approximately one gram or less, of zeolite at atmospheric pressure according to the following procedure. A sample of the zeolite, in the form of pellets or extrudate, is crushed to a particle size about that of coarse sand and mounted in a glass tube. Prior to testing, the zeolite is treated with a stream of air at 1000° F. for at least 15 minutes. The zeolite is then flushed with helium and the temperature is adjusted between 550° F. and 950° F. to give an overall conversion between 10% and 60%. The mixture of hydrocarbons is passed at 1 liquid hourly space velocity (i.e., 1 volume of liquid hydrocarbon per volume of zeolite per hour) over the zeolite with a helium dilution to give a helium to total hydrocarbon mole ratio of 4:1. After 20 minutes on stream, a sample of the effluent is taken and analyzed, most conveniently by gas chromatography, to determine the fraction remaining unchanged for each of the two hydrocarbons.

The "Constraint Index" is calculated as follows:

$$\text{Constraint Index} = \frac{\log_{10}(\text{fraction of n-hexane remaining})}{\log_{10}(\text{fraction of 3-methylpentane remaining})}$$

The Constraint Index approximates the ratio of the cracking rate constants for the two hydrocarbons. Zeolites suitable for the present invention are those having a Constraint Index of 1 to 12. Constraint Index (CI) values for some typical zeolites are:

| CAS | C.I. |
|---|---|
| ZSM-4 | 0.5 |
| ZSM-5 | 8.3 |
| ZSM-11 | 8.7 |

-continued

| CAS | C.I. |
|---|---|
| ZSM-12 | 2 |
| ZSM-23 | 9.1 |
| ZSM-35 | 4.5 |
| ZSM-38 | 2 |
| TMA Offretite | 3.7 |
| Beta | 0.6 |
| H—Zeolon (mordenite) | 0.4 |
| REY | 0.4 |
| Amorphous Silica-Alumina | 0.6 |
| Erionite | 38 |

The above described Constraint Index is an important and even critical definition of those zeolites which are useful in the instant invention. The very nature of this parameter and the recited technique by which it is determined, however, admit of the possibility that a given zeolite can be tested under somewhat different conditions and thereby have different Constraint Indexes. Constraint Index seems to vary somewhat with severity of operation (conversion) and the presence or absence of binders. Therefore, it will be appreciated that it may be possible to so select test conditions to establish more than one value in the range of 1 to 12 for the Constraint Index of a particular zeolite. Such a zeolite exhibits the constrained access as herein defined and is to be regarded as having a Constraint Index of 1 to 12. Also contemplated herein as having a Constraint Index of 1 to 12 and therefore within the scope of the novel class of highly siliceous zeolites are those zeolites which, when tested under two or more sets of conditions within the above-specified ranges of temperature and conversion, produce a value of the Constraint Index slightly less than 1, e.g., 0.9, or somewhat greater than 12, e.g., 14 or 15, with at least one other value of 1 to 12. Thus, it should be understood that the Constraint Index value as used herein is an inclusive rather than an exclusive value. That is, a zeolite when tested by any combination of conditions within the testing definition set forth hereinabove to have a Constraint Index of 1 to 12 is intended to be included in the instant catalyst definition regardless that the same identical zeolite tested under other defined conditions may give a Constraint Index value outside of 1 to 12.

The class of zeolites defined herein is exemplified by ZSM-5, ZSM-11, ZSM-12, ZSM-23, ZSM-35, ZSM-38, and other similar materials. U. S. Pat. No. 3,702,886 describing and claiming ZSM-5 is incorporated herein by reference.

ZSM-11 is more particularly described in U.S. Pat. No. 3,709,979, the entire content of which is incorporated herein by reference.

ZSM-12 is more particularly described in U.S. Pat. No. 3,832,449, the entire content of which is incorporated herein by reference.

ZSM-23 is more particularly described in U.S. Pat. No. 4,076,842, the entire content of which is incorporated herein by reference.

ZSM-35 is more particularly described in U.S. Pat. No. 4,016,245, the entire content of which is incorporated herein by reference.

ZSM-38 is more particularly described in U.S. Pat. No. 4,046,859, the entire content of which is incorporated herein by reference.

The specific zeolites described, when prepared in the presence of organic cations, are substantially catalytically inactive, possibly because the intracrystalline free space is occupied by organic cations from the forming solution. They may be activated by heating in an inert atmosphere at 1000° F. for one hour, for example, followed by base exchange with ammonium salts followed by calcination at 1000° F. in air. The presence of organic cations in the forming solution may not be absolutely essential to the formation of this type zeolite; however, the presence of these cations does appear to favor the formation of this special class of zeolite. More generally, it is desirable to activate this type catalyst by base exchange with ammonium salts followed by calcination in air at about 1000° F. for from about 15 minutes to about 24 hours.

Natural zeolites may sometimes be converted to this type zeolite catalyst by various activation procedures and other treatments such as base exchange, steaming, alumina extraction and calcination, in combinations. Natural minerals which may be so treated include ferrierite, brewsterite, stilbite, dachiardite, epistilbite, heulandite, and clinoptilolite. The preferred crystalline aluminosilicates are ZSM-5, ZSM-11, ZSM-12, ZSM-23, ZSM-35, and ZSM-38, with ZSM-5 being particularly preferred.

In a preferred aspect of this invention, the zeolites hereof are selected as those having a crystal framework density, in the dry hydrogen form, of not less than about 1.6 grams per cubic centimeter. It has been found that zeolites which satisfy all three of these criteria are most desired for several reasons. When hydrocarbon products or by-products are catalytically formed, for example, such zeolites tend to maximize the production of gasoline boiling range hydrocarbon products. Therefore, the preferred zeolites of this invention are those having a Constraint Index as defined above of about 1 to 12, a silica to alumina ratio of at least about 12 and a dried crystal density of not less than about 1.6 grams per cubic centimeter. The dry density for known structures may be calculated from the number of silicon plus aluminum atoms per 1000 cubic Angstroms, as given, e.g., on Page 19 of the article on Zeolite Structure by W. M. Meier. This paper, the entire contents of which are incorporated herein by reference, is included in "Proceedings of the Conference on Molecular Sieves, London, Apr. 1967," published by the Society of Chemical Industry, London, 1968. When the crystal structure is unknown, the crystal framework density may be determined by classical pyknometer techniques. For example, it may be determined by immersing the dry hydrogen form of the zeolite in an organic solvent which is not sorbed by the crystal. Or, the crystal density may be determined by mercury porosimetry, since mercury will fill the interstices between crystals but will not penetrate the intracrystalline free space. It is possible that the unusual sustained activity and stability of this class of zeolites is associated with its high crystal anionic framework density of not less than about 1.6 grams per cubic centimeter. This high density must necessarily be associated with a relatively small amount of free space within the crystal, which might be expected to result in more stable structures. The free space, however, is important as the locus of catalytic activity.

Crystal framework densities of some typical zeolites including some which are not within the purview of this invention are:

| Zeolite | Void Volume | Framework Density |
|---|---|---|
| Ferrierite | 0.28 cc/cc | 1.76 g/cc |
| Mordenite | .28 | 1.7 |
| ZSM-5, -11 | .29 | 1.79 |
| Dachiardite | .32 | 1.72 |
| L | .32 | 1.61 |
| Clinoptilolite | .34 | 1.71 |
| Lauminite | .34 | 1.77 |
| ZSM-4 (Omega) | .38 | 1.65 |
| Heulandite | .39 | 1.69 |
| P | .41 | 1.57 |
| Offretite | .40 | 1.55 |
| Levynite | .40 | 1.54 |
| Erionite | .35 | 1.51 |
| Gmelinite | .44 | 1.46 |
| Chabazite | .47 | 1.45 |
| A | .5 | 1.3 |
| Y | .48 | 1.27 |

When synthesized in the alkali metal form, the zeolite is conveniently converted to the hydrogen form, generally by intermediate formation of the ammonium form as a result of ammonium ion exchange and calcination of the ammonium form to yield the hydrogen form. In addition to the hydrogen form, other forms of the zeolite wherein the original alkali metal has been reduced to less than about 0.5 percent by weight may be used. Thus, the original alkali metal of the zeolite may be replaced by ion exchange with cobalt, but other suitable ions of Groups IB to VIII of the Periodic Table, including, by way of example, nickel, copper, zinc, palladium, calcium or rare earth metals, also may be present.

The crystalline zeolite catalyst is used in intimate combination with a hydrogenating component such as tungsten, iron, vanadium, molybdenum, rhenium, nickel, cobalt, chromium, manganese, or a noble metal such as platinum or palladium where a hydrogenation/-dehydrogenation function is to be performed. Such component can be exchanged into the composition, impregnated therein or physically intimately admixed therewith. Such component can be impregnated in or on the zeolite, such as, for example, by, in the case of platinum, treating the zeolite with a platinum metal-containing ion. Thus, suitable platinum compounds include chloroplatinic acid, platinous chloride and various compounds containing the platinum amine complex.

The compounds of the useful platinum or other metals can be divided into compounds in which the metal is present in the cation of the compound and compounds in which it is present in the anion of the compound. Both types of compounds which contain the metal in the ionic state can be used. A solution in which platinum metals are in the form of a cation or cationic complex, e.g., $Pt(NH_3)_6Cl_4$ is particularly useful.

The amount of the hydrogenation/dehydrogenation component employed is not critical and may range from about 0.01 to about 30 weight percent, preferably 0.1 to 0.5 weight percent, based on the entire catalyst.

In practicing the process of the invention, it may be desirable to incorporate the zeolite in another material resistant to the temperatures and other reaction conditions employed. Such matrix materials include synthetic or naturally occurring substances as well as inorganic materials such as clay, silica and/or metal oxides. The latter may be either naturally occurring or in the form of gelatinous precipitates or gels including mixtures of silica and metal oxides. Naturally occurring clays which can be composited with the modified zeolite include those of the montmorillonite and kaolin families, which families include the subbentonites and the kaolins commonly known as Dixie, McNamee-Georgia and Florida clays or others in which the main mineral constituent is halloysite, kaolinite, dickite, nacrite or anauxite. Such clays can be used in the raw state as originally mined or initially subjected to calcination, acid treatment or chemical modification.

In addition to the foregoing materials, the zeolites employed herein may be composited with a porous matrix materials, such as silica-alumina, silica-magnesia, silica-zirconia, silica-thoria, silica-berylia, silica-titania as well as ternary compositions, such as silica-alumina-thoria, silica-alumina-zirconia, silica-alumina-magnesia and silica-magnesia-zirconia. The matrix may be in the form of a cogel. The relative proportions of finely divided zeolite and inorganic oxide gel matrix may vary widely with the zeolite content ranging from between about 1 to about 99 percent by weight and more usually in the range of about 5 to about 80 percent by weight of the composite. A particularly suitable combination is one containing about 65 weight percent of the zeolite in 35 weight percent of a relatively inactive alumina matrix.

The charge stock can be any alicyclic ketone or alcohol wherein the oxygen is directly connected to a ring carbon atom. By alicyclic is meant a ring-type compound which is at least partially saturated, and may be Mononuclear or polynuclear, that is containing from one to four rings, in which the ring to which the oxygen atom is attached is at least partially saturated. These alicyclic ketones and alcohols include those compounds which contain from one to three oxygen atoms each of which is directly connected to a ring carbon atom. The preferred alicyclic compounds are the mononuclear naphthenic type derivatives. The especially preferred charge stock is cyclohexanone, cyclohexanol, and mixtures of the two. The ring compounds can have one or more groups attached to the ring which do not interfere with the amination reaction, such as lower alkyl having from one to four carbon atoms, phenyl, benzyl, tolyl, xylyl, etc. The charge stock compounds can suitably contain between 4 and 18 carbon atoms per molecule and preferably contain between 6 and 10 carbon atoms. Suitable charge stock compounds include the following without being limited thereto: cyclohexanol, cyclohexanone, cyclohexenol, cyclohexenone, 1,3-cyclohexanediol, 1,4-cyclohexanediol, 1,3-cyclohexanedione, 1,4-cyclohexanedione, 4-methylcyclohexanone, 4-t,butylcyclohexanol, 3,5-dimethylcyclohexanone, 4-phenylcycloexanone, 3-tolylcyclohexanone, cyclopentanol, cyclopentanone, 3-methylcyclopentanol, 2-ketotetralin, 2-(1-cyclohexenyl)-cyclohexanone, 2,6-dicyclohexenylcyclohexanone, etc.

It is preferred to carry out the reaction in the presence of hydrogen. It is advantageous to use partial pressures of hydrogen of from about 100 psi to about 1000 psi. It is advantageous to use a hydrogen to alcohol or ketone molar ratio greater than one. The reaction system may also be partially pressurized with inert gases such as nitrogen, argon.

Inert diluents, such as aliphatic paraffins can be present in the charge stock, if desired, but their presence merely utilizes needed reactor space and reduces the space-time-yield of products. Unsaturated compounds, such as acetylenes, linear or branched olefins, and aromatic type compounds can be tolerated, but are undesirable as they may tend to polymerize, hydrogenate or adversely affect the equilibrium of the reaction.

Production of aromatic amines in the presence of the described catalyst is effected by contact of ammonia with the alcohol or ketone reactant at a temperature between about 150° to about 650° C. and preferably between about 175° and about 250° C. At the higher temperatures, the zeolites of high silica/alumina ratio are preferred. For example, ZSM-5 of 30 $SiO_2/Al_2O_3$ ratio and upwards is very stable at high temperatures. The reaction generally takes place at atmospheric pressure, but the pressure may be within the approximate range of 1 atmosphere to 1000 psig. The relative feed rates, expressed as liquid hourly space velocity of (1) alcohol or ketone and (2) ammonia are generally within the approximate range of 1:0 to 5:0 and preferably between about 1:0 to 4:0. The reaction product may comprise predominately or solely a primary amine. In those instances where some di- or triaromatic amines are formed, together with the water of reaction, they may be separated by any suitable means, such as by distillation or chromatographic separation.

The following example will serve to illustrate the process of this invention without limiting the same:

EXAMPLE

A nickel modified ZSM-5 catalyst having the composition 65% Ni HZSM-5 (0.8% Ni) and 35% alumina binder was prepared and utilized in the conversion of cyclohexanone to aniline at a temperature of 482° C. and a pressure of 200 psig. The ammonia and cyclohexanone reactants were introduced into a reactor of the downflow type at liquid hourly space velocities of 1.3 and 1.0, respectively. The data from this example is set forth below:

| Cyclohexanone Conversion 99.8% | |
|---|---|
| Product Distribution | Wt. % |
| Aniline | 16.2 |
| Diphenylaniline | 2.8 |
| Carbazole | 1.3 |
| Toluidines | 0.9 |
| Pyridines | 1.7 |
| Phenol | 3.2 |
| Alkylphenols | 7.2 |
| Ketones | 1.1 |
| Higher heterocyclics(a) | 57.1 |
| Hydrocarbons | 8.5 |
| | 100.0 |

(a)Mainly 2-phenylindole, 3-methyl benzo-quinoline, acridine.

What is claimed is:

1. In a process for the production of aromatic amines by reaction of alicyclic alcohols, ketones and mixtures thereof with ammonia in the presence of a catalyst, the improvement which comprises utilizing as a catalyst a crystalline silicate zeolite having a silica to alumina ratio of at least about 12 and a constraint index of about 1 to 12.

2. The process of claim 1 wherein said zeolite is characterized by a silica/alumina ratio in excess of 30.

3. The process of claim 1 wherein said reaction is carried out at a temperature between about 150° C. and about 650° C.

4. The process of claim 1 wherein the crystalline silicate is ZSM-5.

5. The process of claim 1 wherein said alcohol is cyclohexanol.

6. The process of claim 1 wherein said ketone is cyclohexanone.

7. The process of claims 2, 3, 4, 5 or 6 wherein the crystalline silicate is dispersed in a matrix.

8. The process of claims 2, 3, 4, 5 or 6 wherein the crystalline silicate is usd in intimate combination with a hydrogenating component.

* * * * *